United States Patent [19]

Barry et al.

[11] 4,198,507

[45] Apr. 15, 1980

[54] THEOPHYLLINE MAGNESIUM SALICYLATE

[75] Inventors: Richard Barry, Bloomfield; Howard Rubin, Rockaway, both of N.J.

[73] Assignee: Hoffmann-La Roche Inc., Nutley, N.J.

[21] Appl. No.: 960,191

[22] Filed: Nov. 13, 1978

[51] Int. Cl.² ........................................... C07D 473/08
[52] U.S. Cl. ................................... 544/267; 424/253
[58] Field of Search ......................................... 544/267

[56] References Cited

FOREIGN PATENT DOCUMENTS 184671  8/1954  Austria ..................................... 544/267

OTHER PUBLICATIONS

The Merck Index, p. 1196 (9006), ninth edition, (1976).

Primary Examiner—Nicholas S. Rizzo
Attorney, Agent, or Firm—Jon S. Saxe; George M. Gould; R. Hain Swope

[57] ABSTRACT

The present invention related to a new compound useful for pharmaceutical purposes, namely, theophylline magnesium salicylate.

1 Claim, No Drawings

THEOPHYLLINE MAGNESIUM SALICYLATE

BACKGROUND OF THE INVENTION

Theobromine (3, 7, dimethyl xanthine) and theophylline (1, 3, dimethyl xanthine) as well known as therapeutic agents because of their effects on the cardiovascular system, their capability of stimulating the central nervous system and for diuresis. These xanthines are closely related chemically and are used therapeutically either as such in the form of their amine salts, e.g. the ethylene diamine salt thereof or most commonly as the so-called double salts thereof with alkali metal salts or alkaline earth metal salts of organic acids, e.g. alkali or alkaline earth metal salts of acetic, gluconic, benzoic or salicylic acid. These double salts may be prepared either to make the therapeutically useful xanthines more water soluble, e.g. for making the water soluble theophylline sodium acetate or for making insoluble complexes, e.g. for making theobromine or theophylline calcium salicylates which said to be better tolerated in the gastrointestinal tract than the parent xanthines.

It is the purpose of the present invention to provide a new chemical compound which has distinct and unique properties and which provides a new form of theophylline which can be used for therapeutic purposes.

DESCRIPTION OF THE PRIOR ART

The prior art discloses methods for the preparation of the so-called xanthine double salts which are prepared with xanthines and alkali or alkaline earth metal salts of organic acids. As illustrative of these prior art procedures, theophylline sodium acetate N. F. $\overline{X}$ is prepared by mixing an equivalent amount each of theophylline and sodium hydroxide, and heating the so-obtained mixture, mixing the so-obtained mixture with an equivalent amount of aqueous sodium acetate and evaporating the mixture to dryness. The resulting theophylline sodium acetate is soluble in water. The soluble theobromine sodium salicylate is made in a similar fashion. See U.S. Dispensatory, Osol and Farrar, 25th edition, 1955, J. B. Lippincott Co., Philadelphia, Pa. pages 1411 and 1409.

Theobromine calcium salicylate N. F. $\overline{X}$ is described in the prior art as being a double salt or complex composed of an equal molecular proportions of theobromine calcium and calcium salicylate. See British Pat. No. 211,166, Oct. 14, 1925 and U.S. Pat. No. 1,547,698 issued July 28, 1925. Both of these patents describe an approach to such double salts which involves dissolving either theobromine or theophylline in aqueous sodium hydroxide, adding to the resulting solution a solution of sodium salicylate followed by a solution of calcium chloride. The precipitate so-obtained is removed and dried giving the desired product.

German Offen. No. 835,146 dated July 1949, teaches adding salicylic acid to theobromine calcium which is suspended in hot water to thereby produce theobromine calcium salicylate. It is obvious then that the theobromine or theophylline calcium salicylate double salts of the patents have the formula $(C_7H_2N_4O_2)$ Ca. $(C_6H_4CHCOO).H_2O$. Theobromine calcium salicylate is known under the trade name Theocalcin (Knoll). The corresponding theophylline calcium salicylate, sold under the trade name Phyllicin (Knoll), is also the double salt of calcium salicylate and calcium theophylline in equimolecular proportions or $(C_7H_7N_4O_2)$ Ca. $(C_6H_4OHCOO).2H_2O$. See the Extra Pharmacopoeia, Martindale, 27th Ed. 1977, Pharmaceutical Press, London, p. 1819; Merck Index, 9th Ed. 1976, Merck & Co., Rahway, N.J. p. 8997.

Both theobromine calcium salicylate and theophylline calcium salicylate show alkaline reactions in aqueous solutions or suspensions.

DESCRIPTION OF THE INVENTION

Theophylline magnesium salicylate of our invention is prepared by adding theophylline to an aqueous solution of magnesium salicylate. On standing, the clear solution which was obtained precipitates a white crystalline solid which is theophylline magnesium salicylate.

EXAMPLE 1

Magnesium salicylate tetrahydrate $(C_6H_4OHCOO)_2Mg.4H_2O)$ 37.1 grams (0.1 mole) was dissolved in 480 ml distilled water and warmed to 40° C. Theophylline anhydrous $(C_7H_8N_4O_2)$ 36.0 grams (0.2 mole) was added and stirred until dissolved. The resulting solution was rapidly filtered and allowed to stand when precipitation of a white crystalline solid began to occur. After standing several hours, the precipitate was filtered off, washed and three 15 ml. portions of cold (5° C.) distilled water. The precipitate was dried at 70° C. for 6 hours. The yield of the product was 61.8 grams (84.5%).

Analysis of the dried product was as follows:

|  | Found | Calculated for: $Tp_2MgS_2 . 5H_2O$ | TpMgS | $TpMgS . 3H_2O$ |
|---|---|---|---|---|
| Theophylline (Tp) | 47.60 | 47.98% | 52.59% | 45.43% |
| Salicylate (S), as salicylic acid | 36.20 | 36.70 | 40.31 | 34.83 |
| Magnesium (Mg) | 3.28 | 3.26 | 7.10 | 6.13 |
| Water (by Karl Fischer) | 12.80 | 12.06 | — | 13.61 |
|  | 99.88 | 100.00% | 100.00% | 100.00 |

As indicated by the analyses, the precipitated product has the formula $Tp_2MgS_2. 5H_2O$. When amounts of magnesium salicylate ranging from 0.5 mole to 2.0 mole were reacted with one mole of theophylline under similar conditions, the precipitated solids after drying showed analyses quite similar to those reported above, indicating that the insoluble product in each case was $Tp_2MgS_2$. Theophylline magnesium salicylate $(Tp_2MgS_2.5H_2O)$ is a white, bitter-tasting, crystalline compound containing about 48% theophylline, 40% magnesium salicylate and 12% water of hydration. It has no definite melting point, is sparingly soluble in water (about 2% at 25° C.) or in alcohol (about 1% at 25° C.). One percent solutions are slightly acidic ($pH_6$).

As further proof that theophylline magnesium salicylate is a definite chemical compound and not a physical mixture of theophylline and magnesium salicylate, the following data were collected:

(a) Ultra-Violet Spectra
(b) Infra-Red Spectra
(c) X-Ray Diffraction Patterns
(d) Thermograms (a) Ultra-Violet Spectra comparing theophylline magnesium salicylate, its components theophylline and magnesium salicylate and a physical mixture of 2 moles of theophylline and (mole of magnesium salicylate does not reveal significant structural changes, the spectra being essentially that exhibited by the individual components.

(b) An Infra-Red spectrogram shows that the aforementioned physical mixture of theophylline and magnesium salicylate is essentially the sum of their individual components. On the other hand, the crystalline theophylline magnesium salicylate shows definite spectral differences from the physical mixture. Besides the difference in the NH stretching region (3120 cm-1), the carbonyl (C=O) band present at 1715 cm-1 of the mixture has disappeared in the spectrum of the compound theophylline magnesium salicylate.

(c) To obtain X-ray diffraction data using a GE XRD-6 spectrogoniometer, samples of the aforesaid physical mixture, its individual components and the compound theophylline magnesium salicylate were irradiated with CuK radiation and the diffraction patterns from r° to 30° 2 0 recorded. The relative peak intensities and inter-planar D-spacings corresponding to the diffraction peaks were calculated using a Wang trigonometric package program adapted to determine 2 0 values from D-values and D-values from 2 0 values. The resulting data show that theophylline magnesium salicylate is a true compound existing in a crystalline habit different from its individual components and a physical mixture of both components.

(d) Thermograms of theophylline magnesium salicylate, its individual components and a 2:1 molar mixture of theophylline and magnesium salicylate were obtained using a Perkin-Elmer DSC 1B scanning calorimeter. Thermal transitions occur in magnesium salicylate and theophylline at 117°–118° C. and 283° C. respectively. Only one thermal transition at 139°–140° C. occurs with the compound theophylline magnesium salicylate. This melt on cooling and re-solidifying was again subjected to thermal analysis and the one transition at 139°–140° C. was again found. The 2:1 molar ratio mixture of theophylline and magnesium salicylate showed two bands, one corresponding to magnesium salicylate (117°–118°) and another at 139°–140° C., the latter probably arises from a reaction between the two components in the molten state to form theophylline magnesium salicylate.

The above data serve to support the fact that theophylline magnesium salicylate is a definite crystalline compound and not a mixture of theophylline and magnesium salicylate.

Since both calcium and strontium are also alkali-earth elements, one would assume that double salts of similar composition would result by interaction of their respective salicylates with theophylline. That this is not the case in exemplified by attempts to make compounds or complexes with (a) calcium salicylate and (b) strontium salicylate under the same conditions used for preparing theophylline magnesium salicylate.

(a) Calcium salicylate, 17.5 grams (0.05 mole) were dissolved in 500 ml. water, then 18.0 grams (0.1 mole) theophylline were dissolved in this solution. No precipitate formed on standing at room temperature; a small amount of solid deposited on standing in the refrigerator overnight was identified as theophylline.

(b) Strontium salicylate, 19.9 grams (0.05 mole) were dissolved in 403 ml. water, then 18.0 grams (0.1 mole) theophylline was dissolved in this solution. No precipitation occurred on standing for several hours. Only a small amount of solid formed overnight in the refrigerator which was identified as theophylline by melting point (276° C.) and mixed melting point with an authentic sample.

No attempts were made to evaporate the aqueous solutions of theophylline and strontium and calcium salicylates and identify the residues since our principle aim was to determine if the reactants would rapidly yield precipitates under the same conditions employed for the reaction between magnesium salicylate and theophylline.

As mentioned earlier, the known theophylline calcium salicylate was stated in the literature (e.g. Merck Index 9th Ed. p. 9006) as being composed of calcium theophylline, Ca $(C_7H_2N_4)_2$) 2 and calcium salicylate in molecular proportions or CaS. To ascertain with certainty that this was the correct formula for theophylline calcium salicylate, we analyzed a commercial sample of this compound (trade name Phyllicin-Knoll) with the following results:

|  | Found | Cal. for TpCaS . 2HO | Cal. for TpCaS |
|---|---|---|---|
| Theophylline (T) | 43.9% | 45.66% | 53.27% |
| Salicylate (S) | 34.1 | 34.94 | 40.77 |
| Calcium | 10.2 | 10.21 | 5.96 |
| Walter (K.F.) | 11.8 | 9.19 | — |
|  | 100.0% | 100.00% | 100.00% |

The results indicate that theophylline calcium salicylate is indeed $TpCaS.2H_2O$ and not $Tp_2CaS_2$. Thus it is not comparable in composition to theophylline magnesium salicylate, $Tp_2MgS_2.5H_2O$.

Pharmaceutical dosage forms containing theophylline magnesium salicylate were prepared as follows:

EXAMPLE 2

A tablet composition useful as a diuretic-broncholytic was made as follows:

|  | mg/Tablet |
|---|---|
| Theophylline magnesium salicylate | 275 |
| Pre-gelatinized starch | 16 |
| Sodium carboxymethyl starch | 12 |
| Magnesium stearate | 2 |
| Purified water, for making a granulation | q.s. |
|  | 305 |

EXAMPLE 3

A tablet useful for treating premenstral tension and dysmenorrhea can be made as follows:

|  | mg/Tablet |
|---|---|
| Theophylline magnesium salicylate | 275 |
| Cinnamedrine | 15 |
| Acetaminophen | 215 |
| Pre-gelatinized starch | 31.5 |
| Sodium carboxymethyl starch | 2.5 |
| Magnesium stearate | 3.0 |

|  | mg/Tablet |
|---|---|
|  | 542 |

One tablet should be given every 4 hours (6 daily) but can be administered to fit the needs of a particular therapeutic situation.

EXAMPLE 4

A capsule formulation can be made as follows:

|  | mg/capsule |
|---|---|
| Theophylline magnesium salicylate | 550 |
| Corn starch | 30 |
| Talc | 30 |
|  | 610 |

EXAMPLE 5

A tablet useful for treating asthma can be made as follows:

|  | mg/tablet |
|---|---|
| Theophylline magnesium salicylate | 275 |
| Ephedrine hydrochloride | 24 |
| Pregelatinized starch | 14 |
| Sodium carboxymethyl starch | 13 |
| Magnesium stearate | 2 |
|  | 336 |

One tablet is given every 4 hours (6 daily) or adjusted to fit the needs of a therapeutic situation.

EXAMPLE 6

A liquid suspension containing 275 mg theophylline magnesium salicylate per 5 ml can be made as follows:

|  | Grams Per 1.0 liter |
|---|---|
| Theophylline magnesium salicylate, micronized crystals | 55 |
| Microcrystalline cellulose RC 591 | 10 |
| Sucrose | 500 |
| Polysorbate 80 | 4 |
| Methyl paraben | 1.0 |
| Propyl paraben | 0.2 |
| Disodium edetate | 0.1 |
| Flavoring agents | qs |
| Coloring agents | qs |
| Purified water | qs to 1.0 liter |

EXAMPLE 7

An ointment suitable for application to the skin can be made as follows:

|  | Grams |
|---|---|
| Theophylline magnesium salicylate, fine powder | 10.0 |
| Hydrophilic ointment USP $\overline{XIX}$ qs to | 100.0 |

PHARMACOLOGICAL ACTIVITY OF THEOPHYLLINE MAGNESIUM SALICYLATE ($T_2MgS_2.5H_2O$)

| 1. Acute Toxicity | $LC_{50}$Mice p.o. (72 hours) |
|---|---|
| Theophylline Magnesium Salicylate | 665 ± 35 mg |
| Theophylline anhydrous | 460 ± 35 mg |
| Magnesium Sailicylate | 1200 ± 53 mg |

The toxicity appears to be a summation of the toxicities of the theophylline and magnesium salicylate entities of the compound which is not unexpected, since the compound contains approximately 48% theophylline and 40% magnesium salicylate.

2. Other Pharmacological Findings

The compound given intravenously to the dog at 4 mg/kg. showed a slight and transient elevation of blood pressure. In the inflamed raw paw (Randall-Selitto test), the compound p.o. at 200 mg/kg. showed expected salicylate (anti-inflammatory and antipyretic) effects of moderate duration (2 to 3 hours). It was, as expected, inactive as an analgesic by the hot plate method.

The compound of the invention is well-tolerated and may readily be used in pharmaceutical preparations, either as such or in combination with other medicinally active agents. The compound can be intermixed with solid carriers or adjuvants or both. In such preparations, the ratio between the therapeutic substance and the carriers and adjuvants may vary between about 1% and about 99%. The preparation may be processed for instance into plain or coated tablets, into gelatin capsules, in liquid suspensions or in ointment form. Pharmaceutically acceptable, organic or inorganic, solid or liquid carriers may be used, suitably for oral (internal) administration or for topical application, in manufacturing the preparations. Gelatin, lactose, sucrose, starch, magnesium stearate, talc, vegetable and animal fats and oils, polyalkylene glycols, and other known carriers for pharmaceuticals, are all suitable for manufacturing preparations of said compound.

The compound of the present invention may be used to provide diuretic and smooth muscle relaxant effects for such conditions as premenstrual tension and asthma. It is also useful as an analgesic agent. It may also be used in combination with the therapeutic agents. For instance, for treatment of premenstrual tension or dysmenorrhea it may be given with an analgesic such as magnesium salicylate, acetaminophen or aspirin and cinnamedrine. In the treatment of asthma, other substances to be given with the compound of the invention include ephedrine and phenobarbital.

We claim:

1. Theophylline Magnesium Salicylate.

\* \* \* \* \*